United States Patent
Shin et al.

(10) Patent No.: US 8,221,715 B2
(45) Date of Patent: Jul. 17, 2012

(54) CARBON-NANOTUBE N-DOPING MATERIAL AND METHODS OF MANUFACTURE THEREOF

(75) Inventors: Hyeon Jin Shin, Suwon-si (KR); Young Hee Lee, Suwon-si (KR); Jaeyoung Choi, Suwon-si (KR); Seonmi Yoon, Yongin-si (KR); Soo Min Kim, Daegu (KR)

(73) Assignee: Samsung Electronics Co., Ltd. (KR)

( * ) Notice: Subject to any disclaimer, the term of this patent is extended or adjusted under 35 U.S.C. 154(b) by 413 days.

(21) Appl. No.: 12/437,221

(22) Filed: May 7, 2009

(65) Prior Publication Data

US 2010/0133480 A1  Jun. 3, 2010

(30) Foreign Application Priority Data

Nov. 28, 2008 (KR) .......................... 10-2008-0119974

(51) Int. Cl.
*H01B 1/00* (2006.01)
(52) U.S. Cl. ............... 423/445 R; 423/460; 252/500; 252/502; 252/510; 977/742; 977/745; 977/746; 977/788; 977/795
(58) Field of Classification Search ........ 252/500–518.1; 423/445 B, 445 R, 460; 977/742, 745, 746, 977/788, 795
See application file for complete search history.

(56) References Cited

U.S. PATENT DOCUMENTS

2008/0099842 A1   5/2008   Gyoujin et al.
2008/0308407 A1*  12/2008  Rostovtsev et al. ...... 204/157.47

FOREIGN PATENT DOCUMENTS

| JP | 06-268199 | 9/1994 |
| KR | 10-2003-0056570 | 7/2003 |
| KR | 10-2006-0029547 | 4/2006 |
| WO | 2008/057108 | 5/2008 |

OTHER PUBLICATIONS

Kim et al. ("Reduction-Controlled viologen in bisolvent as an environmentally stable n-type dopant for carbon nanotubes." JACS, 131, p. 327-331, web publication Dec. 4, 2008).*
Alvaro et al. ("Preparation and photochemistry of single wall carbon nanotubes having covalently anchored viologen units." J Phys Chem B, 109, p. 7692-7697, web publication Mar. 31, 2005).*
Wang et al. (Layer-by-layer assembly of single-walled carbon nanotube-poly(viologen) derivative multilayers and their electrochemical properties. Carbon, 44, p. 2115-2121, web pub May 19, 2006).*

(Continued)

*Primary Examiner* — Mark Kopec
*Assistant Examiner* — Tri V Nguyen
(74) *Attorney, Agent, or Firm* — Cantor Colburn LLP (57) ABSTRACT

A compound containing at least two pyridinium derivatives in its molecular structure and being in a reduced form thereof may be used as a CNT n-doping material. The compound may donate electrons spontaneously to CNTs to n-dope the CNTs, while being oxidized into its stable state. An n-doped CNT that is doped with the CNT n-doping material may maintain a stable n-doped state for a long time without being dedoped even in the air and/or water. Further, the n-doped state may be easily controlled when using the CNT n-doping material.

12 Claims, 7 Drawing Sheets

OTHER PUBLICATIONS

Moonsub Shim, "Polymer Functionalization for Air-Stable n-Type Carbon Nanotube Field-Effect Transistors," J. Am. Chem. Soc., vol. 123, No. 46, Oct. 30, 2001, pp. 11512-11513.

Ali Javey et al., "High Performance n-Type Carbon Nanotube Field-Effect Transistors with Chemically Doped Contacts", Nano Lett., vol. 5, No. 2, Jan. 22, 2005, pp. 345-348.

Christian Klinke et al., "Charge Transfer Induced Polarity Switching in Carbon Nanotube Transistors," Nano Lett., vol. 5, No. 3, Feb. 23, 2005, pp. 555-558.

Seong Jun Kang et al., "High-performance electronics using dense, perfectly aligned arrays of single-walled carbon nanotubes," Nature Nanotechnology, vol. 2, Apr. 2007, pp. 230-236.

* cited by examiner

CARBON-NANOTUBE N-DOPING MATERIAL AND METHODS OF MANUFACTURE THEREOF

CROSS-REFERENCE TO RELATED APPLICATION

This application claims priority to Korean Patent Application No. 10-2008-0119974, filed on Nov. 28, 2008, and all the benefits accruing therefrom under 35 U.S.C. §119, the contents of which in its entirety are herein incorporated by reference.

BACKGROUND

1. Field

This disclosure relates to a carbon nanotube ("CNT") n-doping material, to methods of manufacture thereof and to articles comprising the same.

2. Description of the Related Art

CNTs may be used to manufacture a variety of electronic devices including p-n junction diodes, field-effect transistors, light-emitting devices, complementary metal oxide semiconductors ("CMOS") as well as CNT composites, solar cells, or the like. In order to use CNTs for the purpose, techniques of controlling n-doping and p-doping state may be used.

CNTs are usually in the p-doped state after being prepared because electron depletion occurs due to the use of an acid for the removal of the metal catalysts used in growing CNTs. Thus, oxidizing agents which can withdraw electrons from the CNTs may be used for controlling the p-doping state. Examples of oxidizing agents include hydrochloric acid, sulfuric acid, nitric acid, or metal salts examples of which are gold chloride, silver nitrate, or the like.

In order to n-dope CNTs, reducing agents, which can donate electrons to CNTs may be used. Examples of the reducing agents may include alkali metals including potassium, sodium, and the like, or reducing polymers including polyethyleneimide, amine-containing molecules including hydrazine, polyaniline, and the like.

SUMMARY

Disclosed herein is a carbon nanotube ("CNT") n-doping material including a compound that includes at least two pyridinium derivatives in its molecular structure, the compound being in a reduced form thereof.

Disclosed herein is a CNT n-doping method including n-doped CNTs with the CNT n-doped material.

Disclosed herein is a n-doped CNT with the CNT n-doping material.

The compound that includes at least two pyridinium derivatives in its molecular structure and being in a reduced form thereof may be used as a CNT n-doping material. CNTs n-doped with the CNT n-doping material may maintain a stable n-doped state for a long time without being redoped even in the air and/or water. Further, the n-doped state may be easily controlled when using the CNT n-doping material.

Disclosed herein too is a composition comprising carbon nanotubes; and a carbon nano-tube n-doping material comprising a compound that comprises at least two pyridinium derivatives in its molecular structure, the compound being in a reduced form thereof.

Disclosed herein too is a composition comprising a n-doped CNT; the n-doped CNT being doped with a CNT n-doping material comprising a compound containing at least two pyridinium derivatives in its molecular structure, the compound being in a reduced form thereof.

BRIEF DESCRIPTION OF THE DRAWINGS

The above and other aspects, features and advantages of the invention will be more apparent by describing in further detail exemplary embodiments thereof with reference to the attached drawings, in which:

FIGS. 4a and 4b are $I_{sd}$-$V_g$ graphs showing the effect of viologen on n-doping of CNTs, where the X axis represents $V_g$ in volts ("V") and the Y axis represents $I_{sd}$ in microamperes ("μA").

FIG. 5b shows the position of $I_{min}$ according to the amount change of the solution of reduced viologen. In FIG. 5b, the X axis represents the used amount (number of droplets) of the solution of reduced viologen, the Y axis in the right side represents $I_{sd}$ (A), and the Y axis in the left side represents the position of $I_{min}$ (V);

FIGS. 8a-8d are graphs showing n-doping effects according to types of viologen compounds [BV (1,1'-dibenzyl-4,4'-bipyridinium dichloride), MV (methyl viologen dichloride hydrate) and EV (ethyl viologen diperchlorate)].

DETAILED DESCRIPTION

Aspects, advantages, and features of exemplary embodiments of the invention and methods of accomplishing the same may be understood more readily by reference to the following detailed description of embodiments and the accompanying drawings. The exemplary embodiments of the invention may, however, may be embodied in many different forms, and should not be construed as being limited to the embodiments set forth herein. Rather, these embodiments are provided so that this disclosure will be thorough and complete and will fully convey the concept of the invention to those skilled in the art, and the exemplary embodiments of the invention will only be defined by the appended claims. Like reference numerals refer to like elements throughout the specification.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items.

It will be understood that, although the terms first, second, third, etc., can be used herein to describe various elements, components, regions, layers and/or sections, these elements, components, regions, layers and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the exemplary embodiments of the invention.

Spatially relative terms, such as "below," "lower," "upper" and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device can be otherwise oriented (rotated 90 degrees or at other orientations) and the spatially relative descriptors used herein interpreted accordingly.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation can result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

In exemplary embodiments, a pyridinium derivative compound in its reduced state may be used as a novel carbon nanotube (CNT) n-doping material. The pyridinium derivative compound may be a compound containing at least two pyridinium derivatives in its molecular structure and being in a reduced form. In one embodiment, the reduced form of the compound may be obtained by the reduction of the nitrogen atom on a benzene ring of at least one pyridinium derivative.

The compound containing at least two pyridinium derivatives in its molecular structure may have a low redox potential and be artificially reduced so as to be in a relatively unstable state. The reduced unstable compound may donate electrons spontaneously to CNTs while being oxidized into a relatively stable state. When a conjugated structure is inserted as a bridge between the two or more pyridinium derivatives in the molecular structure of the compound, the compound in its reduced state may be more unstable than when it is in the unreduced state. In the reduced state, it donates electrons more spontaneously to CNTs.

An example of a compound containing at least two pyridinium derivatives in its molecular structure may include viologen containing bipyridinium derivatives.

Viologen is a 4,4'-bipyridyl derivative having diquaternary amine groups. Viologen may undergo a change in polarity by redox reaction.

Figure 1A:
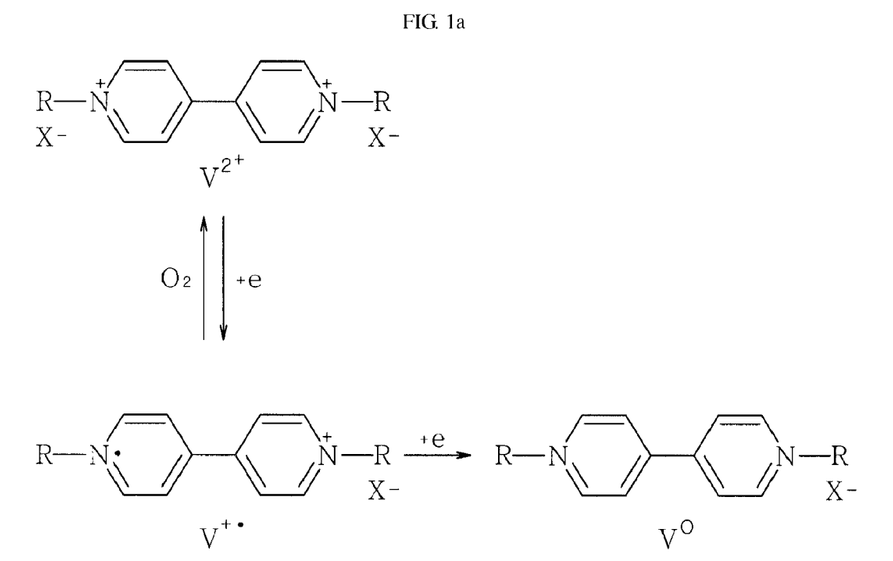
FIGS. 1a and 1b are schematic views showing viologen in its oxidized state and reduced state.
Figure 1B:
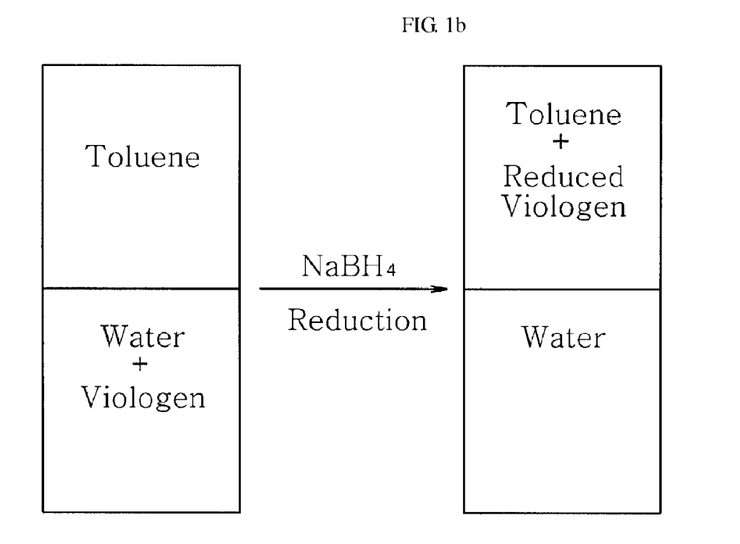

FIGS. 1a and 1b are schematic views showing viologen in its oxidized state and reduced state respectively and the behavior thereof.

Referring to FIG. 1a, the initially oxidized form of polar viologen ($V^{2+}$) may accept electrons to be reduced ($V^+$, $V^0$) into a less polar or into a non-polar state. Herein, the reduction site may be either or both of the two nitrogen atoms on the benzene rings of the two pyridinium derivatives.

The reduced viologen may have affinity to a non-polar solvent, while viologen in its oxidized state has affinity to water. Referring to FIG. 1b, it is shown that the polar viologen initially having affinity to water may accept electrons to be reduced into a non-polar state and thus have affinity to a non-polar solvent.

Since the reduced viologen is more unstable than its initial state, the reduced viologen may donate electrons to the surroundings and be converted into its more stable state. When viologen is artificially reduced and then put together with CNTs, the reduced viologen may react with the surrounding CNTs and spontaneously donate electrons to the CNTs, which reconverts the reduced unstable viologen into its initial stable state.

Figure 2:
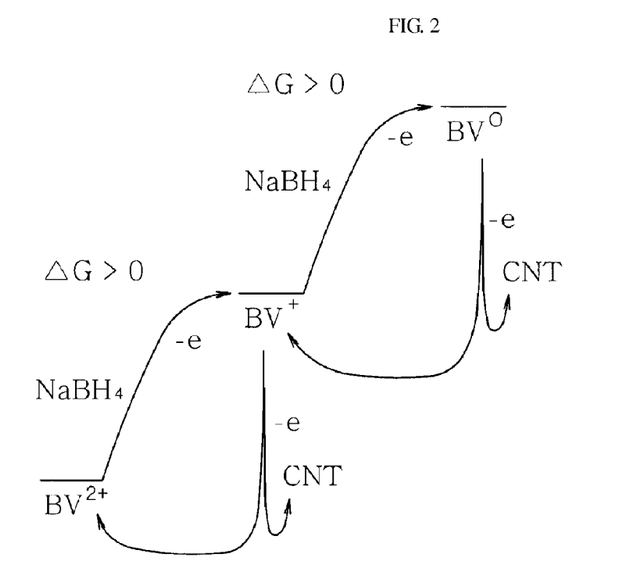
FIG. 2 is a schematic view showing the Gibbs free energy difference derived from different reduced states of 1,1'-dibenzyl-4,4'-bipyridinium dichloride (BV), one of the viologen compounds.

FIG. 2 is a schematic view showing the Gibbs free energy difference derived from different reduced states of 1,1'-dibenzyl-4,4'-bipyridinium dichloride (BV), one of the viologen compounds used in exemplary embodiments.

Referring to FIG. 2, a reducing agent such as sodium borohydride ($NaBH_4$) is used to reduce the nitrogen atom of the benzene ring of each pyridinium derivative of $BV^{2+}$ so that $BV^{2+}$ is reduced to $BV^+$ (partially reduced form) and to $BV^0$ (totally reduced form). When the reduced viologen is blended with CNTs, each reduced form of viologen may be converted back to its stable state by donating electrons to the surrounding CNTs.

Thus, the partially or totally reduced form of viologen may be used as a CNT n-doping material. Totally reduced viologen may donate more electrons and thus provide a higher degree of CNT n-doping as compared to the partially reduced viologen.

Suitable examples of viologen may include 1,1'-dibenzyl-4,4'-bipyridinium dichloride (BV), methyl viologen dichloride hydrate (MV), ethyl viologen diperchlorate (EV), 1,1'-dioctadecyl-4,4'-bipyridinium dibromide (DBDB), or the like.

Meanwhile, viologen may further include a molecular structure capable of conjugation between the two pyridine structures. In other words, when the two pyridine structures located at both terminal positions and a conjugatable structure is inserted as an intermediate bridge between the two pyridine structure, the pyridine at each terminal position may be in the state of oxidation number 0 due to resonance. The presence of such a conjugatable structure may allow the reduced viologen to donate electrons more spontaneously to CNTs.

The viologen compounds containing the conjugatable molecular structure between both pyridinium structures may be referred to as 'extended viologens'.

Suitable examples of the conjugatable molecular structure in the extended viologens may include aryl, alkenyl, alkynyl, or the like. Examples of suitable aryls may include phenyl. Examples of suitable alkenyls may include ethenyl. Examples of suitable alkynyls may include thiophenyl. Further, the extended viologens may include a bipolaron of dioctyl bis(4-pyridyl)biphenyl viologen.

However, viologen compounds are not limited to the above-mentioned examples.

In an exemplary embodiment, a reducing agent may be used to reduce the compound containing at least two pyridinium derivatives in its molecular structure. Suitable examples of reducing agents may include at least one of $NaBH_4$, $LiAlH_4$, $NaH$, $CaH_2$, hydrazine, or the like. Any reducing agent capable of reducing the compound may be used. The degree of reduction may be controlled, for example, by adjusting the amount of the reducing agent added to the compound.

In an exemplary embodiment, N-doping of CNTs may be performed by contacting the reduced form of the compound with the CNTs to be n-doped so that the compound may donate electrons to the CNTs.

In one embodiment, the reducing compound may be blended with a solvent to form a solution and the solution may then be used to contact the CNTs. That is, a solution containing the reduced form of the compound may be prepared and then the solution may be contacted with the CNTs that are to be n-doped. Then, the CNTs disposed in the solution (containing the reduced form of the compound) may be heated to remove the solvent in the solution.

A method for reducing viologen and a method for providing the reduced viologen to CNTs will be described hereinafter as a non-limiting example.

As shown in FIG. 1b, water and a non-polar solvent which can be separated from water when mixed with water (e.g. toluene as shown in FIG. 1b) may be added sequentially to viologen to perform phase separation, and a reducing agent may be added thereto to obtain a non-polar solvent phase.

The non-polar solvent may be one which can be separated from water when mixed with water in order to draw the reduced compound (e.g. reduced viologen etc.) from water. The non-polar solvent may be an organic solvent except ketone based compound, amid based compound, alcohol based compound since they may not be separated from water when mixed with water. Suitable examples of the non-polar solvent may include at least one of alkanes, aromatic compounds, glycol ethers, glycol ether acetates, acetates, halogen compounds or nitrogen compounds.

As mentioned above, suitable examples of the reducing agent may include at least one of $NaBH_4$, $LiAlH_4$, $NaH$, $CaH_2$, hydrazine, or the like. However, the reducing agent that may be used herein is not limited to the above examples and any materials may be used as long as they are capable of reducing viologen. The reduction may lead the viologen to be a part of the non-polar solvent phase such as an organic phase which may include toluene.

Then, CNTs to be n-doped may be treated with the resultant solution containing the reduced viologen to perform n-doping of CNTs, followed by heating to remove the solvent.

When CNTs are n-doped with the compound containing at least two pyridinium derivatives in the reduced state, stable n-doping may be obtained. The CNTs may not have to be de-doped even when left in the air and/or water. The stable n-doping state may be maintained for a long time, which means that the compound may be useful as a CNT n-doping material.

The amount of the reduced compound used in the doping of the CNTs may affect the n-doped state of CNTs. In other words, a larger amount of the reduced compound may allow a higher degree of n-doping of CNTs. This means that the degree of n-doping may be easily controlled by adjusting the amount of the reduced compound.

A method for adjusting the amount of the reduced compound, for example, reduced viologen will be described hereinafter as a non-limiting example.

For example, the reduced viologen may be dissolved into a solvent to provide a solution, and then the amount of the resultant solution may be adjusted on a basis of number of droplets, for example, one droplet, two droplets, or the like, or on a basis of concentration of the reduced viologen in the solution. Since such methods are simple in adjusting the amount of the reduced viologen, the n-doped state of CNTs may be easily controlled by using the methods.

In one embodiment, the reduced compound may be added to the solvent to have about 1 mM to about 100 mM, based on the total weight of the solution.

In an exemplary embodiment, the reduced compound may be added to the solvent to have about 10 mM to about 50 mM based on the total weight of the solution.

The compound containing at least two pyridinium derivatives and being in its reduced state, for example, the reduced viologen may allow n-doping of CNTs so that the compound may be used for various industrial fields requiring n-doping of CNTs. Non-limiting examples of the applications may include various devices such as p-n junction diodes, carbon nanotube field-effect transistor (CNT-FET), complementary metal oxide semiconductors (CMOS), or the like.

The examples and experiments will now be described. The following examples and experiments are for illustrative purposes only and not intended to limit the scope of this disclosure.

Experiment 1: Effect of Reduced Viologen on N-Doping of CNTs

To investigate the effect of the reduced viologen (1,1'-dibenzyl-4,4'-bipyridinium dichloride, 'BV') on n-doping of CNTs, a solution of reduced viologen is prepared in advance. As shown in FIG. 1b, water and toluene are added sequentially to the oxidized form of viologen ($BV^{2+}$) to perform phase separation.

The oxidized form of viologen ($BV^{2+}$) is treated with a reducing agent, $NaBH_4$, to obtain the reduced viologen (Refer to FIGS. 1a and 1b). The conversion of the oxidized form into the reduced form is checked through the absorption peak at 405 nm. The concentration of the viologen solution used in the subsequent experimental procedure is set at 50 mM. Making the initial concentration of the $BV^{2+}$ in the water be 50 mM and adding the toluene of the same amount with the water and adding the reducing agent $NaBH_4$ of 1 equivalent amount or more to obtain the reduced viologen (BV), the reduced viologen (BV) have the same concentration of 50 mM in the toluene likewise the initial concentration of the $BV^{2+}$ in the water while the reduced viologen (BV) wholly moves to toluene.

Figure 3:
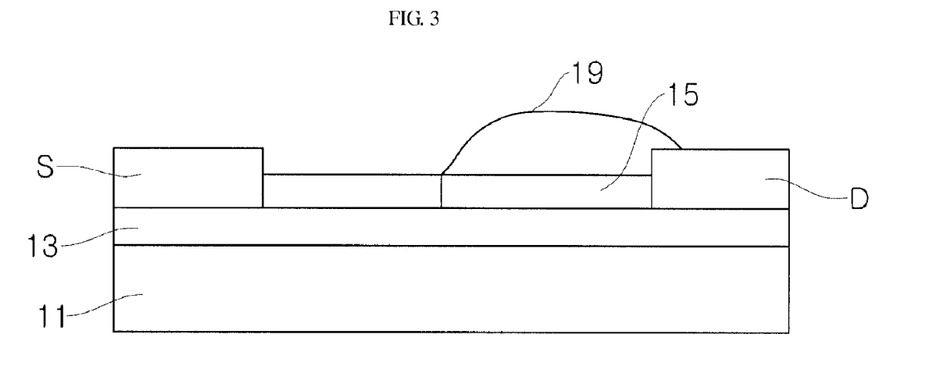
FIG. 3 is an exemplary schematic view showing a carbon nanotube field-effect transistor ("CNT-FET")

To investigate the effect on n-doping of CNTs, a CNT-FET is manufactured. FIG. 3 is a schematic view showing the CNT-FET used in the experiment.

Referring to FIG. 3, an $SiO_2$ interlayer dielectric 13 is formed on an Si back gate 11 doped with $N^+$, and a source electrode S and a drain electrode D are formed thereon. In addition, a CNT channel 15 grown by thermal chemical vapor deposition ("TCVD") is formed between the source electrode S and the drain electrode D.

One droplet (100 µL) of the solution of reduced viologen 19 prepared as described above is dropped onto the CNT channel portion by using a micropipette, and then heated at 110° C. for 3 minutes.

Figure 4A:
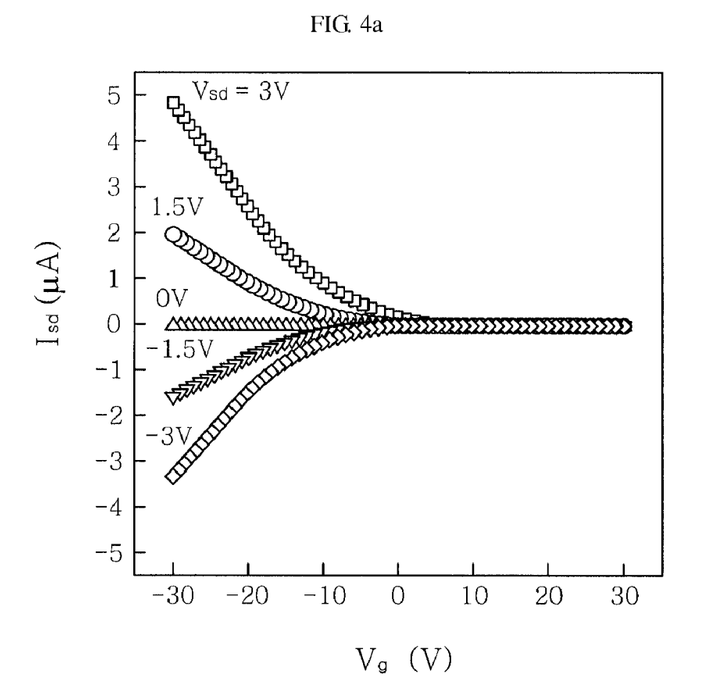
FIG. 4a is a graph before n-doping with viologen and FIG. 4b is a graph after n-doping with the reduced viologen.
Figure 4B:
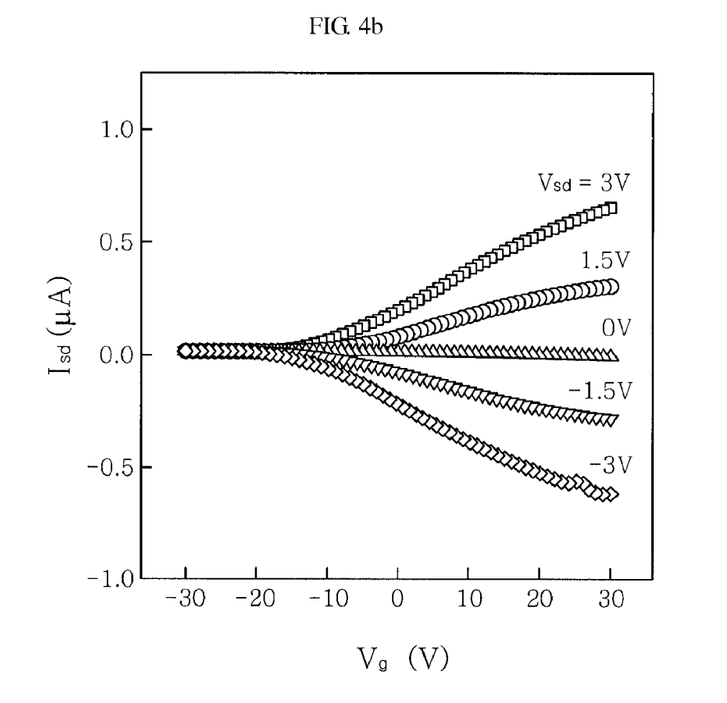

FIGS. 4a and 4b are $I_{sd}$-$V_g$ graphs showing an effect of viologen on n-doping of CNTs in the experiment, where the X axis represents $V_g$ (V) and the Y axis represents $I_{sd}$ (µA). FIG. 4a is a graph before n-doping with viologen and FIG. 4b is a graph after n-doping with the reduced viologen. It is to be noted that the subscript "sd" in the expression $I_{sd}$ stands for "source to drain". $I_{sd}$ therefore represents the source to drain current. In a similar manner, the subscript "g" in the expression $V_g$ stands for "gate". The expression $V_g$ therefore stands for gate voltage.

Referring to FIGS. 4a and 4b, conversion from the initial p-doped state into the n-doped state occurs in the CNTs after treating the CNTs with the reduced viologen.

Experiment 2: N-Doped State According to Amount of Solution of Reduced Viologen

In this experiment, the amount of the solution of reduced viologen dropped onto the CNT channel portion is increased to investigate variations of the n-doped state of CNTs according to the amount of the solution of reduced viologen. Herein, the concentration of the solution of reduced viologen is set at 1 millimolar ("mM"), and the same CNT-FET as described in Experiment 1 is used.

Figure 5A:
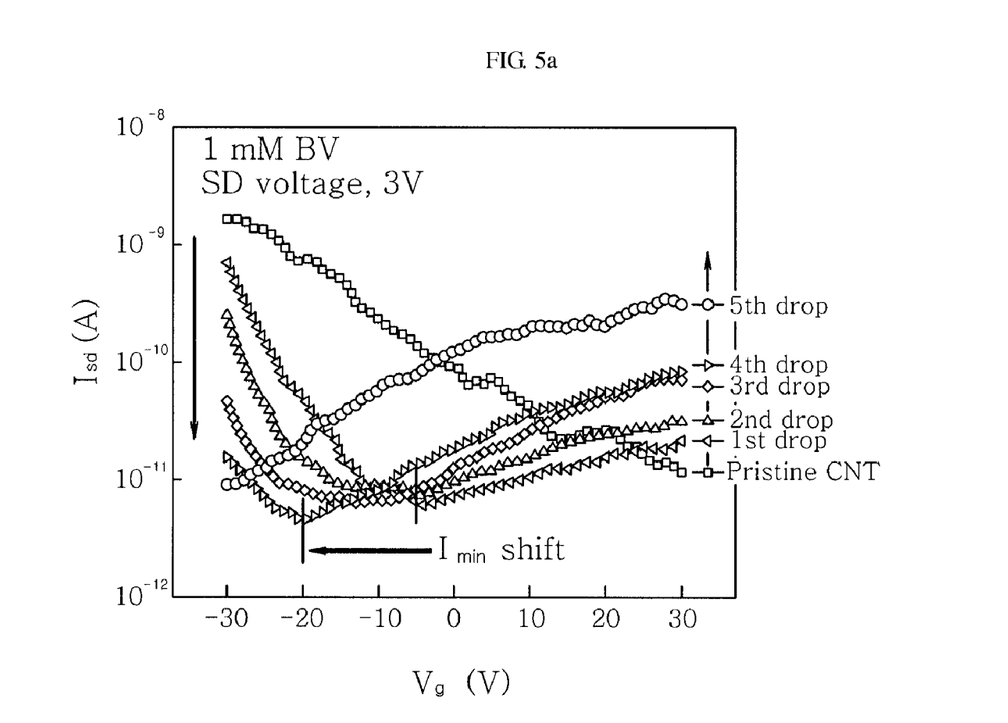
FIG. 5a is an $I_{sd}$-$V_g$ graph showing the n-doped state variation versus the amount of change of a solution of reduced viologen, where the X axis represents $V_g$ (V) and the Y axis represents $I_{sd}$ in Amperes ("A")

FIG. 5a is an $I_{sd}$-$V_g$ graph showing the n-doped state variation according to an amount of change of a solution of reduced viologen in the experiment, where the X axis represents $V_g$ (V) and the Y axis represents $I_{sd}$ (A).

Referring to FIG. 5a, as the amount of the solution of reduced viologen increases (from $1^{st}$ drop to $5^{th}$ drop), the p-doped state is converted into the n-doped state, while $V_{th}$ corresponding to each droplet number moves in the direction of negative bias. When the point where the p-doped state is converted into the n-doped state at each $V_{th}$ is denoted as $I_{min}$, a shift of $I_{min}$ occurs toward the left side. $V_{th}$ stands for threshold voltage Therefore, the degree of n-doping may be controlled by adjusting the amount of the solution of reduced viologen. This means that the reduced viologen may have excellent controllability for the n-doping of CNTs.

Figure 5B:
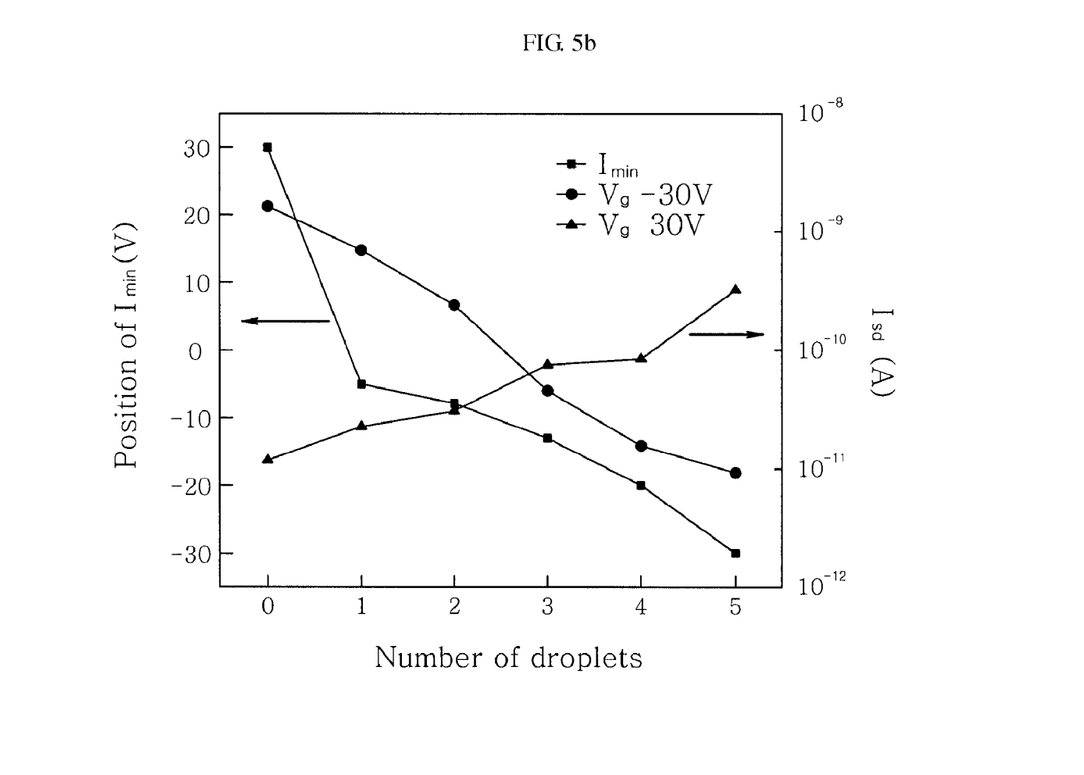
FIG. 5b is an $I_{sd}$-$V_g$ graph showing variations in $I_{sd}$ when the amount of change of the solution of reduced viologen as shown in FIG. 5a is represented in the X axis and $V_g$ is −30 V and 30 V. Further.

FIG. 5b is an $I_{sd}$-$V_g$ graph showing variations in $I_{sd}$ when the amount of change of the solution of reduced viologen as shown in FIG. 5a is represented in the X axis and $V_g$ is $-30$ V and 30 V. Further, FIG. 5b shows the location of the minimum current ($I_{min}$) and its dependency on the amount of change of the solution of reduced viologen. The FIG. 5b represents the change in the minimum current with the number of drops of the solution of the reducing compound. In FIG. 5b, the X axis represents the used amount (number of droplets) of the solution of reduced viologen, the Y axis in the right side represents $I_{sd}$ (A), and the Y axis in the left side represents the position of $I_{min}$ (V).

Referring to FIG. 5b, when observing $I_{sd}$ at a gate voltage of $-30$ V, the on-current drops to an off-current. On the other hand, when observing $I_{sd}$ at a gate voltage of 30 V, an off-current increases to an on-current. Further, as the droplet number increases, the position of $I_{min}$ moves toward the negative voltage, i.e., in the direction of negative bias.

[Experiment 3: Doping Stability in Air]

In this experiment, stability of the n-doped state of CNTs is investigated with time. Herein, the concentration of the solution of reduced viologen is set at 50 mM, and the same CNT-FET as described in Experiment 1 is used.

Figure 6:
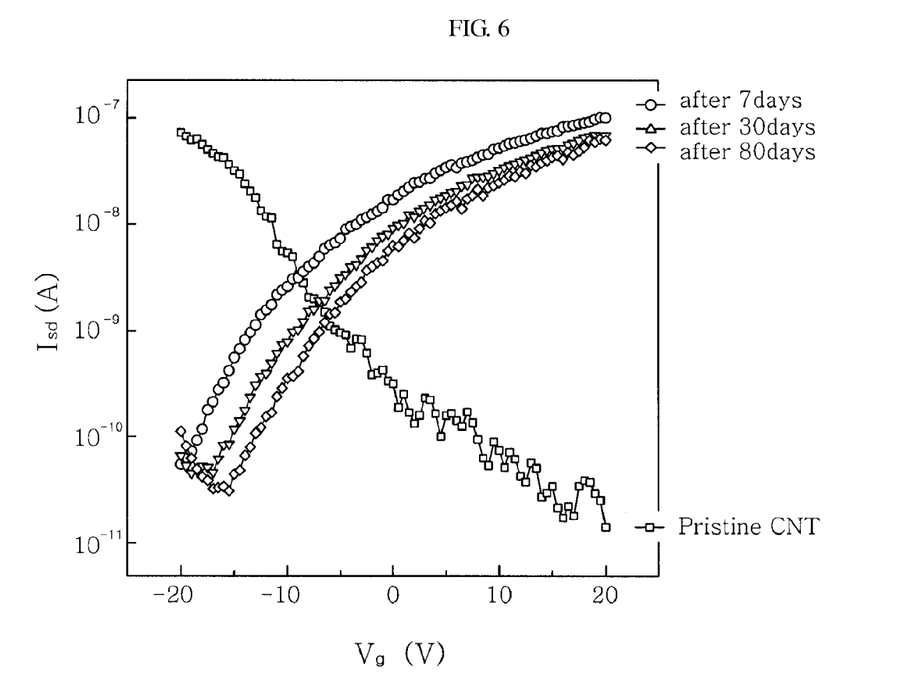
FIG. 6 is a graph showing the n-doped states right after dropping one droplet of the solution of reduced viologen to CNT-FET, and after a period of 7 days, 30 days and 80 days in the air, where the X axis represents $V_g$ (V) and the Y axis represents $I_{sd}$ (A)

FIG. 6 is a graph showing the n-doped states right after dropping one droplet of the solution of reduced viologen onto the CNT-FET. The FIG. 6 depicts the change in the current $I_{sd}$ with the passage of time. Specifically, it depicts the current after a lapse of 7 days, 30 days and 80 days of being exposed to air, where the X axis represents $V_g$ (V) and the Y axis represents $I_{sd}$ (A).

Referring to FIG. 6, even after the lapse of 80 days, the CNTs still display n-type behavior although it shows a slight decrease in the current level. This suggests that the stability of the n-doped CNTs is maintained in the air even for a long time.

[Experiment 4: Doping Stability in Water]

In this experiment, stability of the n-doped state of CNTs is investigated in water. Herein, the concentration of the solution of reduced viologen is set at 50 mM, and the same CNT-FET as described in Experiment 1 is used.

Figure 7:
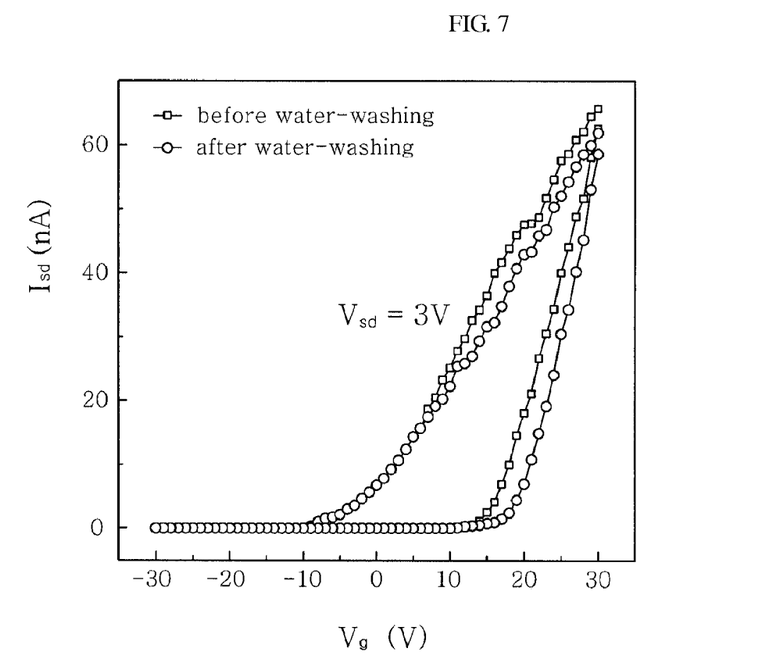
FIG. 7 is a graph showing the n-doped states before and after washing with water, after one droplet of the solution of reduced viologen is dropped on to the CNT-FET and the solvent is removed therefrom, where the X axis represents $V_g$ (V), the Y axis represents $I_{sd}$ (nA) and $V_{sd}$ is set to be 3 V.

FIG. 7 is a graph showing the n-doped states before and after washing with water, after one droplet of the solution of reduced viologen is dropped to CNT-FET and the solvent is removed therefrom in the experiment, where the X axis represents $V_g$ (V), the Y axis represents $I_{sd}$ in nanoamperes (nA) and $V_{sd}$ is set to be 3 V.

Referring to FIG. 7, the doped state is relatively well maintained before and after washing with water. In other words, the doped state undergoes no change even under the direct contact with water. This suggests that stability of the n-doped CNTs is maintained even in water.

[Experiment 5: N-Doping of CNTs According to Types of Viologen]

In this experiment, n-doping of CNTs according to types of viologen compound [BV (1,1'-dibenzyl-4,4'-bipyridinium dichloride), MV (methyl viologen dichloride hydrate) and EV (ethyl viologen diperchlorate)] is investigated. Herein, the concentration of the solution of reduced viologen is set at 50 mM, and the same CNT-FET as described in Experiment 1 is used. The solvent that is used to solubilize the viologen is toluene.

Figure 8A:
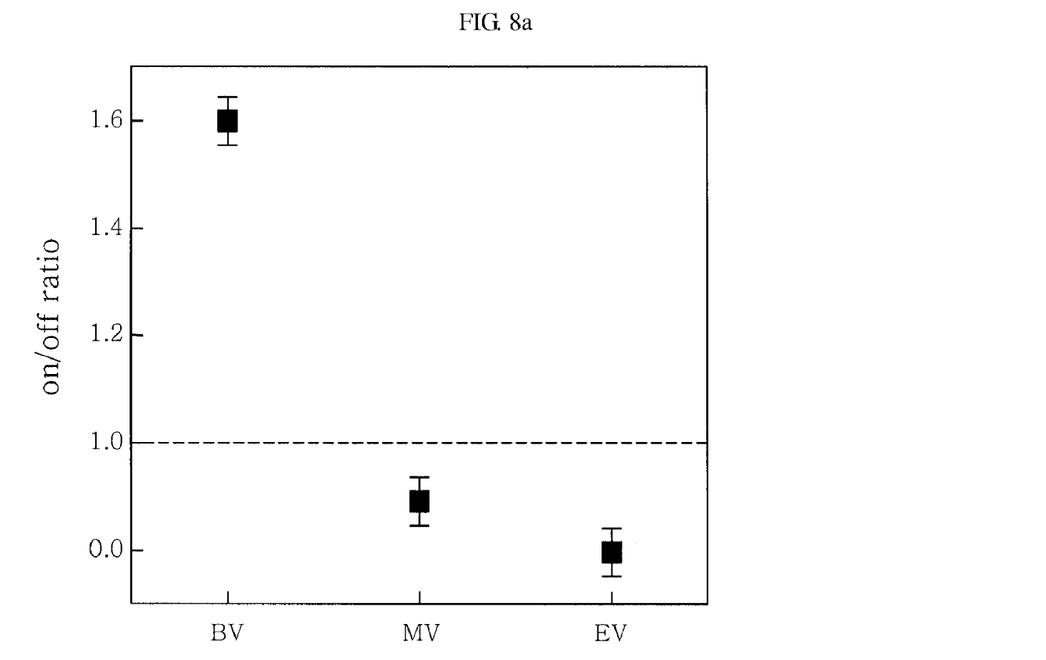
FIG. 8a is a graph showing the on/off ratio for each type of viologen, where the X axis represents respective viologen compounds and the Y axis represents the on/off ratio (dimensionless) in each viologen compound. Further.
Figure 8B:
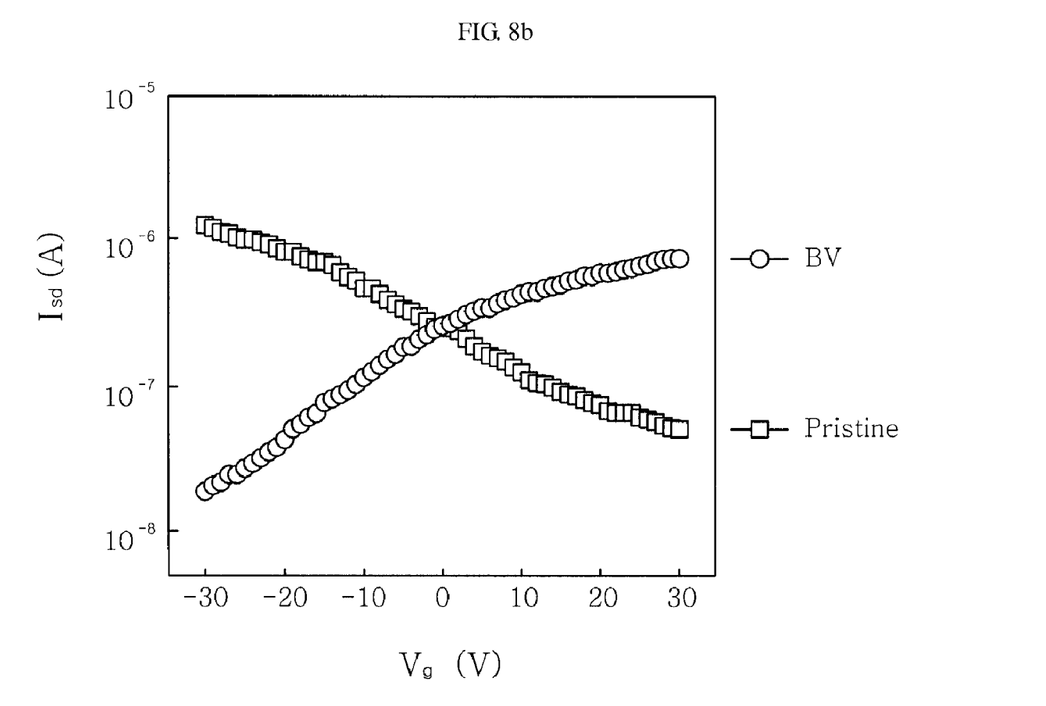
FIGS. 8b-8d are $I_{sd}$(A)-$V_g$ (V) graphs according to types of viologen compounds (BV, MV and EV), where the X axis represents $V_g$ (V) and the Y axis represents $I_{sd}$ (A).
Figure 8C:
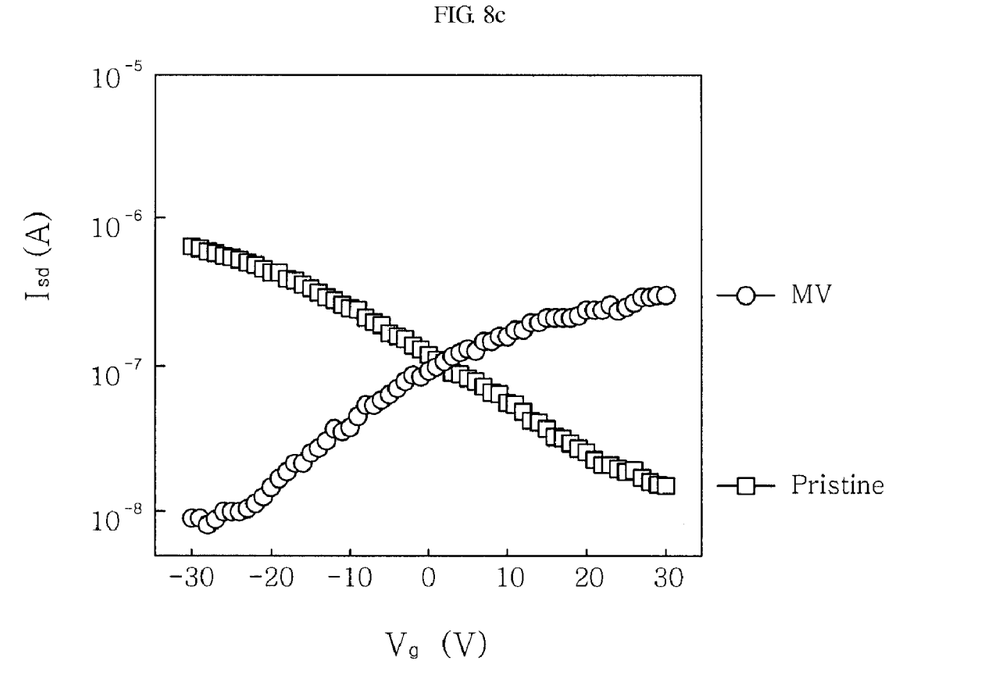
Figure 8D:
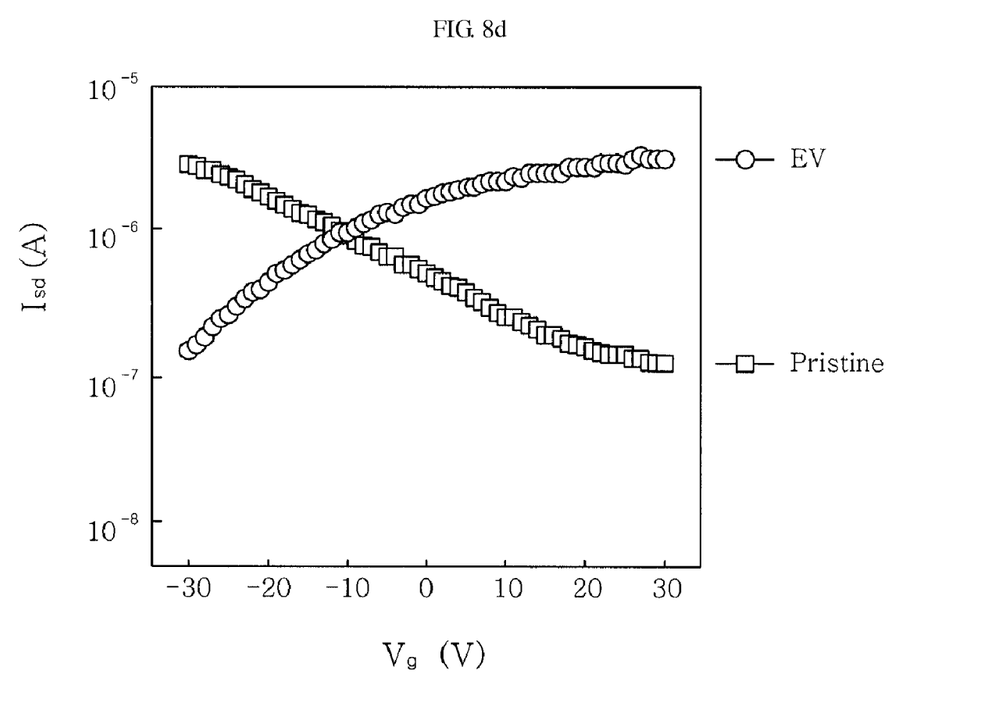

FIGS. 8a-8d are graphs showing n-doping effects according to types of viologen compounds [BV, MV and EV] in the experiment. FIG. 8a is a graph showing the on/off ratio of each type of viologen, where the X axis represents respective viologen compounds and the Y axis represents the on/off ratio (dimensionless) in each viologen compound. Further, FIGS. 8b-8d are $I_{sd}$ (A)-$V_g$ (V) graphs according to types of viologen compounds (BV, MV and EV), where the X axis represents $V_g$ (V) and the Y axis represents $I_{sd}$ (A).

Referring to FIGS. 8a-8d, in the case of viologens, MV and EV, off-current increases due to being doped heavily, resulting in a decrease in the on-off ratio. However, viologen BV has best efficiency in terms of the on/off ratio. Further, all of the viologen solutions of BV, MV and EV allow the CNTs to undergo a shift from the initial p-doped state into the n-doped state.

While the exemplary embodiments have been shown and described, it will be understood by those skilled in the art that various changes in form and details may be made thereto without departing from the spirit and scope of the invention as defined by the appended claims.

In addition, many modifications can be made to adapt a particular situation or material to the teachings of the invention without departing from the essential scope thereof. Therefore, it is intended that the present invention not be limited to the particular exemplary embodiments disclosed as the best mode contemplated for carrying out this invention, but that the present invention will include all embodiments falling within the scope of the appended claims.

What is claimed is:

1. A method for n-doping of carbon nano-tubes comprising:
   n-doping carbon nano-tubes with a carbon nano-tube n-doping material comprising a compound containing at least two pyridinium derivatives in its molecular structure, the compound being in a reduced form thereof.

2. The method according to claim 1, wherein the compound is viologen.

3. The method according to claim 2, wherein the method further comprises contacting the carbon nano-tubes that are to be doped with a solution containing a reduced viologen.

4. The method according to claim 3, wherein the method further comprises heating the carbon nano-tubes provided with the solution to remove a solvent in the solution.

5. The method according to claim 3, wherein the solution is prepared by a method comprising:
   adding water and a non-polar solvent sequentially to viologen to obtain a phase separated solution;
   adding a reducing agent to the solution; and
   obtaining a non-polar solvent phase from the solution.

6. The method according to claim 3, wherein the non-polar solvent is at least one selected from the group consisting of alkanes, aromatic compounds, glycol ethers, glycol ether acetates, acetates, halogen compounds, nitrogen compounds and a mixture thereof.

7. The method according to claim 3, wherein the reducing agent is at least one selected from the group consisting of $NaBH_4$, $LiAlH_4$, $NaH$, $CaH_2$, hydrazine and a mixture thereof.

8. The method according to claim 1, wherein an amount of viologen in the solution is adjusted to control the n-doped state of the carbon nano-tubes.

9. The method according to claim 1, wherein the reduced form of the compound is obtained by the reduction of the nitrogen atom on a benzene ring of at least one pyridinium derivative.

10. The method according to claim 2, wherein the viologen is at least one selected from the group consisting of 1,1'-dibenzyl-4,4'-bipyridinium dichloride, methyl viologen dichloride hydrate, ethyl viologen diperchlorate, 1,1'-dioctadecyl-4,4'-bipyridinium dibromide, dioctyl bis(4-pyridyl)biphenyl viologen, and a combination thereof.

11. The method according to claim 2, wherein the viologen comprises a molecular structure capable of conjugation between bipyridyl structure.

12. The method according to claim 11, wherein the molecular structure capable of conjugation comprises aryl, alkenyl, alkynyl or a combination thereof.

* * * * *